(12) United States Patent
Hoerner et al.

(10) Patent No.: US 6,365,278 B1
(45) Date of Patent: Apr. 2, 2002

(54) MULTILAYER MATERIAL, PROCESS OF PREPARATION AND APPLICATIONS

(75) Inventors: Pierre Hoerner, Horbourg-Wihr; Gérard Riess, Mulhouse; René Guy Busnel, Bievres; André Cheymol, Dange Saint Romain, all of (FR)

(73) Assignee: Hutchinson, Paris (FR)

( * ) Notice: Subject to any disclaimer, the term of this patent is extended or adjusted under 35 U.S.C. 154(b) by 0 days.

(21) Appl. No.: 09/455,917

(22) Filed: Dec. 7, 1999

Related U.S. Application Data

(62) Division of application No. 08/769,736, filed on Dec. 19, 1996, now Pat. No. 6,020,070.

(30) Foreign Application Priority Data

Dec. 20, 1995 (FR) .............................. 95 15166

(51) Int. Cl.[7] .......................... A41D 19/00; B32B 25/08
(52) U.S. Cl. ............................ 428/423.1; 428/423.9; 428/424.2; 428/424.8; 428/409; 428/500; 428/515; 428/516; 428/517; 428/520; 428/522; 2/161.7; 2/168; 128/918; 604/168; 604/349
(58) Field of Search ..................... 428/423.1, 423.9, 428/424.2, 424.8, 409, 500, 515, 516, 517, 520, 522; 2/161.7, 168; 128/844, 918; 604/57, 168, 349

(56) References Cited

U.S. PATENT DOCUMENTS

| 5,128,168 A | 7/1992 | Shlenker et al. ............. 427/2.3 |
| 5,338,565 A | 8/1994 | Shlenker et al. ........... 427/2.25 |
| 5,357,636 A | 10/1994 | Dresdner, Jr. et al. ....... 2/161.7 |
| 5,369,155 A | 11/1994 | Asmus ........................ 524/55 |
| 6,020,070 A | * 2/2000 | Hoerner et al. .......... 428/423.1 |

FOREIGN PATENT DOCUMENTS

| EP | 306389 | 7/1992 |
| WO | WO 95/17453 | 6/1995 |

OTHER PUBLICATIONS

Encyclopedia of Polymer Science and Engineering (Sup. vol. 674–689) (1985).

* cited by examiner

Primary Examiner—D.. Lawrence Tarazano
(74) Attorney, Agent, or Firm—Morrison & Foerster LLP

(57) ABSTRACT

Multilayer elastomer films (multilayer material) comprising at least one continuous layer, carrying an active chemical substance (such as corrosion inhibitors, lubricants or alternatively biocides for medical use), inserted between inert elastomer barrier layers, processes for the preparation and various applications of these films. The multilayer polymeric material comprises at least one layer A composed of a gel which is reversible or non-reversible, as a function of the temperature, and which carries at least one active chemical substance x, and at least two barrier layers E comprising a synthetic elastomer e, the said layers being held together by a polymeric bonding agent y incorporated in at least one of the said layers A or E and/or by an independent bonding layer Z comprising a polymer z and/or by a chemical or physical treatment of at least one of the said layers A or E.

42 Claims, 3 Drawing Sheets

MULTILAYER MATERIAL, PROCESS OF PREPARATION AND APPLICATIONS

Figure 1:
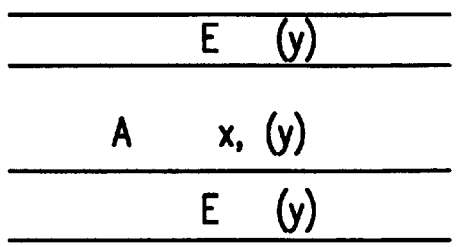

This application is a division of U.S. application Ser. No. 08/769,736, filed Dec. 19, 1996, now U.S. Pat. No. 6,020,070.

The present invention relates to multilayer elastomer films (multilayer material) comprising at least one continuous layer carrying active chemical substance (such as corrosion inhibitors, lubricants or alternatively biocides with a medical use) inserted between inert elastomer barrier layers; it also relates to the processes for the preparation and to the various applications of these films.

The various elastomer materials commonly used in the medical or paramedical field can be modified so as to be combined with active chemical substances having a protective effect during the use of these materials (gloves, fingerstalls, condoms, and the like), as illustrated in European Patent 306,389 or International Application WO 95/17453, on behalf of the Applicant Company, which describe elastomer films enclosing a dispersion of at least one active chemical substance, which dispersion being either in the liquid form (International Application WO 95/17453) or contained in microcapsules, the walls of which are ruptured under the effect of frictional or shear forces (European Patent 306,389).

However, the preparation of elastomer films according to the methods described in the above-mentioned applications and patents exhibits a number of disadvantages, which relate either to the product itself, that is to say the film, or to the process for obtaining the film.

disadvantages related to the product:

the major disadvantage of the films according to either of the two abovementioned methods is the non-homogeneity of the distribution of the active chemical substances within the polymeric material, due to the fact that the chemical substance is dispersed in the polymeric material in the form of droplets or microcapsules.

This non-uniformity in the distribution of the active chemical substances is reflected by gaps in active chemical substance, which constitute a risk in the context of the desired protection, even if this risk is statistically very low;

the microcapsules contained in the elastomer films according to European Patent 306,389 can exhibit difficulties in rupturing, to release their active substances, during the perforation of the said films;

the elastomer films containing liquid inclusions according to International Application WO 95/17453 involve macromolecular stabilizers of grafted or sequenced copolymer (block copolymer) type which are relatively expensive.

disadvantages related to the process:

in the case of International Application WO 95/17453, the preparation of films from a dispersion of active chemical substance is conditioned by the stability of the bath containing the dispersion, itself a function of the active substance (virucide, for example) content, which constitutes a limiting factor;

likewise, in U.S. Pat. No. 306,389, the production of microcapsules, of controlled size, requires the use of a complex process, particularly as regards controlling the thickness and porosity of the wall;

the preparation of films according to either of the two methods is accompanied, in all cases, by emission of organic vapours; indeed, the elastomers are always used in more or less concentrated solution form in organic solvents.

Consequently, on continuing its research, the Applicant Company has set itself the aim of developing a new type of elastomer material corresponding better to practical requirements than the array of elastomers of the prior art, in particular in that it includes at least one active chemical substance, in the desired proportions, in the form of a continuous layer and not of a dispersion or of an emulsion, which makes it possible to avoid the problems related to the dispersion and/or emulsification stage (stability of the emulsion bath, expense of the stabilizing polymers, presence of gaps), and in that it makes it possible to obtain a flexible and elastic multilayer material which is particularly well suited to the preparation of gloves, fingerstalls or condoms from which the active substance x is only released in the event of the material tearing.

Moreover, the process for the preparation of the material according to the present invention can be carried out entirely or partially in aqueous medium.

The subject of the present invention is a multilayer polymeric film (multilayer material), characterized in that it comprises at least one layer A composed of a gel which is reversible or non-reversible, as a function of the temperature, and which carries at least one active chemical substance x, and at least two barrier layers E comprising a synthetic elastomer e, the said layers being held together by a polymeric bonding agent y incorporated in at least one of the said layers A or E and/or by an independent bonding layer Z comprising a polymer z and/or by chemical or physical treatment of at least one of the said layers A or E.

Chemical treatment is understood to mean either a grafting or a chemical attack using an acid, for example sulfuric acid, and physical treatment is understood to mean a bombardment of the surface of the film with ions or electrons: corona or plasma treatment, or photons: ultraviolet treatment.

Gels which are non-reversible, as a function of the temperature, are formed chemically, that is to say by crosslinking by covalent bonding, which takes place by addition of a crosslinking agent ic (irreversible crosslinking agent) and/or by thermal or photochemical activation, such as, for example, under the effect of ultraviolet radiation, whereas gels which are reversible as a function of the temperature are formed either physically, that is to say by interaction of hydrogen bond, Van der Waals or dipole-dipole type or by formation of crystalline domains or complexes. Such reversible gels can also, in certain cases, involve a crosslinking agent rc (reversible crosslinking agent).

In the case of reversible gels, a transition takes place at a critical temperature (Ttrans) at which the physical interactions disappear; the gel-liquid transformation corresponds to this temperature.

According to an advantageous embodiment of the said layer A, when it is composed of a reversible gel, the latter essentially comprises a structuring polymer c, at least one active chemical substance x and a solvent $s_a$; in addition, it can contain a bonding agent y and a reversible crosslinking agent rc. The combination forms a flexible and elastic layer A.

In certain cases, the structuring polymer c also acts as solvent $s_a$.

According to an advantageous arrangement of this embodiment, the said reversible gel exhibits a gel-liquid transition temperature (Ttrans) of between 0° C. and 120° C., preferably of between 20° C. and 85° C. and more particularly between 20° C. and 700° C.

According to another advantageous arrangement of this embodiment, the structuring polymer c of the layer A is a polymer which is immiscible with the elastomer e, preferably of hydrophilic type and compatible with the active chemical substance, alone or in solution in a solvent $s_a$.

According to an advantageous form of this arrangement, the structuring polymer c is selected from the group consisting of synthetic polymers of acrylic or vinyl type, such as poly(acrylic acid) and polyvinyl alcohol, or of natural origin, such as gelatin, gums, pectin, alginates, polypeptides, polyureas, heparinoids and poly(gluconic acid), as well as certain cellulose derivatives, such as methyl cellulose, hydroxyethyl cellulose, hydroxypropyl cellulose and carboxymethyl cellulose, or certain starch derivatives and crystallizable or partially crystallizable polymers, such as, for example, polyethers.

According to another advantageous arrangement of this embodiment, the crosslinking agent rc is selected from the group consisting of (i) certain boron derivatives, such as boric acid or borax, (ii) certain divalent metals, such as zinc or calcium, and (iii) certain trivalent metals, such as aluminium, in alumina hydrate, aluminium sulphate or certain aluminium hydroxides, or chromium, in chromium oxide; it is used as crosslinking agent for the structuring polymer c preferably containing hydroxyl functional groups, such as polyvinyl alcohol, and acts by formation of physical bonds between the chains of the structuring polymer c.

According to another advantageous embodiment of the said layer A, when it is composed of a non-reversible gel, the latter essentially comprises a structuring polymer c, a crosslinking agent rc, at least one active chemical substance x and a solvent $s_a$; in addition, it can contain a bonding agent y. The combination then forms a flexible and elastic layer A.

In certain cases, the structuring polymer c also acts as solvent $s_a$.

According to an advantageous arrangement of this embodiment, the structuring polymer c is a polymer which is immiscible with the elastomer e, preferably of hydrophilic type and compatible with the active chemical substances x, alone or in solution in a solvent $s_a$.

According to an advantageous form of this arrangement, the said structuring polymer c is selected from the group consisting of (i) polymers of natural origin, such as gelatin, gums, pectins, alginates, polypeptides, polyureas, heparinoids and poly(gluconic acid) or certain cellulose derivatives, such as methyl cellulose, hydroxyethyl cellulose, hydroxypropyl cellulose and carboxymethyl cellulose, or certain starch derivatives and (ii) synthetic polymers, such as polyethyleneimine, poly(acrylic acid), polyvinyl alcohol, which are alone or as interpenetrated networks, polyacrylamides and their derivatives, polyvinylpyrrolidone, polydimethylsiloxane or poly(vinyl ethers) such as poly(vinyl methyl ether).

According to another advantageous arrangement of this embodiment, the crosslinking agent ic is selected, for the polymers c containing hydroxyl functional groups, from aldehydes or dialdehydes of low or high molecular weight, such as, for example, glyoxal, or other compounds, such as urea-formaldehyde or melamine-formaldehyde derivatives, and, for the polymers containing hydroxyl, carboxyl or amine functional groups, from prepolymers containing isocyanate functional groups and generally from any other compound capable of reacting chemically with the structuring polymer c.

In accordance with the invention, the layer A additionally comprises, whatever the gel (reversible or non-reversible):

at least one active chemical substance x, selected from compounds capable of causing virtually instantaneous denaturation of proteins on simple contact, either by chemical reaction or by a physico-chemical effect, such as by modification of the surface tension. This family of compounds comprises, inter alia, biocides; the said active chemical substance x must be suitable for the structuring polymer c and for the other constituents of the layer A, in order to avoid any possibility of chemical reaction between them.

According to an advantageous arrangement, the said active chemical substance is a quaternary ammonium, preferably dimethyldidecylammonium (Bardac®), biguanides, phthalaldehyde, phenol derivatives, formaldehyde, non-ionic surfactants containing at least one polyoxyethylene sequence, hexamidine, iodinated compounds, for example the polyvinylpyrrolidone-iodine complex, non-ionic surfactants with a virucidal activity, sodium and potassium dichromates and hypochlorites or charged polymers, such as polyelectrolytes exhibiting biocidal activities, such as poly (acrylic acid), poly(divinylbenzyltrimethyl-ammonium chloride), the divinyl ether-maleic anhydride copolymer, polyethyleneimines, polyetheramines, polyureas and polypeptides, which are used alone or as mixtures.

In certain cases, the active chemical substance x also acts as solvent $s_a$.

a solvent $s_a$, selected from the group consisting of (i) compounds of low volatility, such as polyols, preferably from ethylene glycol, propylene glycol or glycerol, and more generally polyethylene glycols which are liquid at room temperature and with a molecular mass of between 62 (ethylene glycol) and 750 daltons (PEG 750), or water when it is included in the structuring polymer c, (ii) volatile solvents, such as alcohols or ketones of low molecular weight, non-cyclic or cyclic ether compounds, such as tetrahydrofuran, (iii) dimethyl-formamide or dimethyl sulphoxide, or (iv) water (elimination by evaporation), which are used alone or as mixtures.

The layer A, in addition, optionally comprises:

a bonding agent y, chosen from polymers containing both at least one poly A sequence compatible with the layer A and at least one poly E sequence compatible with the layer E which are selected from the group consisting of di-block copolymers, of poly A-block-poly E type, tri-block copolymers of poly E-block-poly A-block-poly E (EAE) type, of poly A-block-poly E-block-poly A (AEA) type, of poly A-block-poly E-block-poly F (AEF) type or of poly A-block-poly F-block-poly E (AFE) type, and grafted copolymers of poly A-grafted-poly E or poly E-grafted-poly A type or of poly A-grafted-poly E and -poly F type, it being possible for the poly F sequence to be compatible with the layer A or with the layer E, or from adhesives of acrylic, silicone or polyurethane type.

The poly A sequences are chosen from the group which comprises polyoxyethylene, polyvinylpyridine, poly(acrylic acid)s, polyvinyl alcohol and quaternized polyvinylpyridine and the poly E sequences are chosen from the group which comprises polydienes, polyolefins, polyoxypropylene and polydimethylsiloxane.

As examples of polydienes or polyolefins, the following may be cited: polybutadiene, polyisoprene, hydrogenated polybutadiene, hydrogenated polyisoprene, polystyrene or poly-4-tert-butylstyrene.

Mention may in particular be made, among the grafted structures containing poly A, poly E and poly F sequences, of:

as poly F sequences, acrylic chains, for example, as poly E sequences, alkyl chains, for example, and as poly A sequences, polyoxyethylene chains, for example.

These structures correspond to certain grafted polymers sold by the company Goldschmidt under the trade name "Brinoil LE®".

According to another embodiment of the said multilayer material, the said gel layer A comprises:

when the gel is reversibly crosslinked:
between 0 and 98%, preferably between 25 and 98%, of solvent $s_a$ with respect to the gel,
between 0.1 and 74%, preferably between 1 and 74%, of structuring polymer c with respect to the gel,
between 1 and 80%, preferably between 1 and 74%, of the said active chemical substance x with respect to the gel and
between 0 and 0.1% of crosslinking agent rc crosslinking agent content by mass/combined cibstutyebts);

when the gel is non-reversibly crosslinked:
between 0 and 98%, preferably between 25 and 98%, of solvent $s_a$ with respect to the gel,
between 0.1 and 74%, preferably between 1 and 74% of structuring polymer c with respect to the gel,
between 1 and 80%, preferably between 1 and 74%, of the said active chemical substance x with respect to the gel and
between 0.0001 and 0.1% of crosslinking agent ic (crosslinking agent content by mass/combined constituents).

A bonding agent y can be added in proportions by mass of 0.01 to 25% with respect to the gel; the proportions of solvent $s_a$ are consequently adjusted.

Also in accordance with the invention, the said multilayer material comprises, as layer E, a synthetic elastomer e, selected in a non-limiting way from polybutadiene, polyisoprene, acrylic polymers, polychloroprene, polyurethane, copolymers based on chlorobutadiene and methacrylic acid or based on ethylene and vinyl acetate, or SBR (Styrene Butadiene Rubber), SBS (styrene-butadiene-styrene), SIS (styrene-isoprene-styrene) or SEBS (styrene-ethylene-butylene-styrene) copolymers, and optionally a bonding agent y as defined above.

The elastomer e can be used either in the form of a solution in an organic solvent $s_a$ or in the form of an aqueous dispersion (latex).

Also in accordance with the invention, the said multilayer material comprises, as bonding layer Z, a polymer z selected from the group consisting of (i) the di-block, tri-block or grafted copolymers described in the preceding arrangements (copolymer used as bonding agent y), (ii) polymers of acrylic or vinyl type, such as, for example, vinyl acetate or vinyl laurate, (iii) diene polymers containing nitrile functional groups, such as NBR (nitrile-butadiene-rubber), polyurethanes and certain polyesters or polyamides and (iv) copolymers of the same type as those selected for the layer E, which are treated in order to render them compatible with the layer A, either chemically by grafting, such as SEBS treated with maleic anhydride, or by chemical attack of SBS or SIS with a sulfuric acid solution, or alternatively physically, by bombardment of the surface of the film using ions or electrons: corona and plasma treatment, or with photons: ultraviolet treatment.

The polymer z can be used either in the form of a solution in an organic solvent $s_a$ or in the form of an aqueous dispersion (latex).

Such polymeric films or multilayer materials, formed from at least one continuous gel layer A, optionally containing a bonding agent y, and from at least two elastomer barrier layers E, optionally containing a bonding agent y, which are held together using the said bonding agent y and/or using an independent bonding layer Z, exhibit, unexpectedly, a flexible and elastic structure which is particularly well suited to the preparation of gloves, fingerstalls or condoms. The latter provide the wearer of the said material, in particular during medical examinations or surgical operations or in dentistry, with effective protection against infectious agents which are transmittable by the blood, in particular in the event of tearing or even simply of splits in the elastomer membrane which could result in contamination of the wearer of the said material, the use of which is therefore not without risk in the absence of the multilayer material according to the invention.

Another subject of the present invention is processes for the preparation of a multilayer material according to the invention comprising at least one layer A composed of a reversible gel, as defined above, and at least two barrier layers E comprising a synthetic elastomer e, the said layers being held together by a polymeric bonding agent y incorporated in at least one of the said layers A or E and/or by an independent bonding layer Z comprising a polymer z:

The "reversible gel layer A" process $\hat{1}$ comprises:
1) the preparation of a first elastomer barrier layer E, which may or may not carry bonding agent y, by dissolution of a polymer e, as defined above, in a solvent $s_e$, selected from the group consisting of (i) aromatic, aliphatic and alicyclic hydrocarbons, for example paraffin hydrocarbons, cyclohexane, benzene, toluene, xylene, tetralin or decalin, (ii) petroleum fractions, (iii) other more polar solvents, such as alcohols or ketones of low molecular weight, (iv) non-cyclic or cyclic ether compounds, such as tetrahydrofuran, (v) water, or (vi) dimethylformamide or dimethyl sulphoxide, which are used alone or as mixtures, spreading the said solution over an appropriate substrate and evaporation of the solvent $s_e$; the film-forming can be accompanied by a crosslinking stage, such as, for example, a vulcanization. The solvent is water in the case where the polymer e is used in the form of a dispersion (latex);
2) the preparation of at least one layer A according to the following process, when the gel is formed spontaneously by bonds of physical type;
preparation of a solution by mixing at least one active chemical substance x, optionally in a solvent $s_a$, with a structuring polymer c and optionally a bonding agent y at a temperature greater than the transition temperature Ttrans corresponding to the gel-liquid transition, which temperature Ttrans is between 20° C. and 120° C. (film-forming of the mixture), followed by
spreading the said solution over the layer obtained in Stage 1) and cooling to a temperature of less than Ttrans; the film-forming can be accompanied by emission of solvent $s_a$;
3) the spreading of a succession of layers A and E according to a desired order, which layers A and E are optionally separated by bonding layers Z and are prepared in accordance with Stages 1) and 2) and
4) the preparation and the spreading or a final elastomer barrier layer E which may or may not carry a bonding agent y, by evaporation of the solvent $s_e$ or water, this stage optionally being followed by a crosslinking stage, such as, for example, a vulcanization.

The "reversible gel layer A" Process $\hat{2}$ comprises:
1) the preparation of a first elastomer barrier layer E in accordance with Stage 1) of the "reversible gel layer A" Process $\hat{1}$;
2) the preparation of at least one layer A, according to the following process, when the addition of a crosslinking agent rc is necessary for the formation of the reversible gel (crosslinking agent rc introduced simultaneously with the mixture comprising the polymer c):

preparation of a solution by mixing at least one active chemical substance x, optionally in a solvent $s_a$, with a structuring polymer c and optionally a bonding agent y at a temperature greater than the transition temperature Ttrans corresponding to the gel-liquid transition, which temperature Ttrans is between 20° C. and 120° C., introduction, simultaneously with the mixture comprising the structuring polymer c, the active chemical substance x, the solvent $s_a$ and optionally the bonding agent y, of a crosslinking agent rc, for example by spraying: the crosslinking takes place rapidly and induces the formation of the film;

spreading the said solution over the layer obtained in 1), followed by cooling and rapid crosslinking;

3) the spreading of a succession of layers A and E according to a desired order, which layers A and E are optionally separated by bonding layers Z and are prepared in accordance with Stages 1) and 2) and 4) the preparation and the spreading of a final elastomer barrier layer E in accordance with Stage 1).

The "reversible gel layer A" Process 3 comprises, in Stage 2), the incorporation of the crosslinking agent rc in a volatile solvent itself forming a film.

Another subject of the present invention is processes for the preparation of a multilayer material according to the invention comprising at least one layer A composed of a non-reversible gel, as defined above, and at least two barrier layers E comprising a synthetic elastomer e, the said layers being held together by a polymeric bonding agent y incorporated in at least one of the said layers A or E and/or by an independent bonding layer Z comprising a polymer z:

The "non-reversible gel layer A" Process 1 comprises:

1) the preparation of a first elastomer barrier layer E, which may or may not carry bonding agent X, by dissolution of a polymer e in accordance with the invention in a solvent $s_e$, as defined above, spreading the said solution over an appropriate substrate and evaporation of the solvent $s_e$; and optionally crosslinking;

2) the preparation of at least one layer A according to the following process (incorporation of the crosslinking agent ic directly in the solution):

preparation of a solution by mixing at least one active chemical substance x, optionally in a solvent $s_a$, with a structuring polymer c and optionally a bonding agent y, incorporation of a crosslinking agent ic directly in the said solution, spreading the said solution over the layer obtained in Stage 1) (film-forming), initiation of the crosslinking by the photochemical and/or thermal route or alternatively by contact with a crosslinking accelerator;

3) the spreading of a succession of layers A and E according to a desired order, which layers A and E are optionally separated by bonding layers Z and are prepared in accordance with Stages 1) and 2) and 4) the preparation and the spreading of a final elastomer barrier layer E in accordance with Stage 1).

The "non-reversible gel layer A" Process 2 comprises:

1) the preparation of a first elastomer barrier layer E in accordance with Stage 1) of the "non-reversible gel layer A" Process 1;

2) the preparation of at least one layer A according to the following process (introduction of the crosslinking agent ic simultaneously with the mixture);

preparation of a solution by mixing at least one active chemical substance x, optionally in a solvent $s_a$, with a structuring polymer c and optionally a bonding agent y, introduction, simultaneously with the mixture comprising the polymer c, the active chemical substance x, the solvent $s_a$ and optionally the bonding agent y, of a crosslinking agent ic, for example by spraying; the crosslinking takes place rapidly and induces the formation of the film;

spreading the said solution over the layer obtained in Stage 1), followed by rapid crosslinking, inducing the formation of the film;

3) the spreading of a succession of layers A and E according to a desired order, which layers A and E are optionally separated by bonding layers z and are prepared in accordance with Stages 1) and 2) and 4) the preparation and the spreading of a final elastomer barrier layer E in accordance with Stage 1).

In accordance with the invention, the superimposition of various films A prepared with various active chemical substances x makes it possible simultaneously to obtain the effects of the said chemical substances without combining them.

According to an advantageous embodiment of the said processes, the bonding layer Z is prepared by evaporation of the solvent $s_z$ or of water from a mixture comprising a polymer z, as defined above, in solution in a solvent $s_z$, selected from the group which comprises aromatic, aliphatic and alicyclic hydrocarbons, more polar compounds, such as ethers such as tetrahydrofuran, ketones, dimethylformamide, dimethyl sulphoxide, or alcohols, and water or a mixture of intermediate polarity.

According to an advantageous arrangement of this embodiment, the bonding layer Z is subjected to a crosslinking initiated photochemically, such as, for example, under the effect of ultraviolet radiation, and accelerated thermally or alternatively chemically, such as, for example, by oxidation or using a crosslinking agent. The solvent is water in the case where the polymer z is used in the form of a dispersion (latex).

As an alternative form, in the case where the said layers are held together by a chemical or physical treatment, the process for the preparation of the said multilayer material comprises, after the spreading of a layer A and/or of a layer E over an appropriate substrate, a chemical or physical treatment as defined above.

As another alternative form, the multilayer material according to the invention comprising a non-reversible gel as layer A comprises a stage of preparation of the structuring polymer c by in situ polymerization from a mixture of one or a number of monomers m and of at least one active chemical substance x, by the thermal route or by the photo-chemical (ultraviolet radiation) or radiochemical ($^{60}$Co cobalt source) route.

According to an advantageous embodiment of this alternative form, the said mixture additionally comprises at least one of the following additional components: an initiator i, one or a number of solvents $s_a$, a thickener f, a crosslinking agent ic or a bonding agent y.

According to an advantageous arrangement of this embodiment, the said monomers m are preferably selected from the group consisting of acrylates and their derivatives, such as acrylic acid, hydroxyethyl methacrylate or methyl methacrylate, acrylamides, acrylamines and their derivatives, or vinyl pyrrolidone.

According to an advantageous form of this arrangement, the number of monomers used is between 1 and 10, preferably between 1 and 4.

In accordance with this alternative form:

in the case of a polymerization initiated thermally, the initiator i is selected from the group consisting of the family of peroxides, such as benzoyl peroxide, the family of azonitriles, such as azobisisobutyronitrile, or redox pairs, such as the pair $S_2O_8/S_2O_5$;

in the case of a polymerization initiated photochemically, the initiator i is selected from the group consisting of the family of acetophenones, benzoin derivatives or the family of peroxides.

According to another advantageous arrangement of this embodiment, the thickener f is selected from the group consisting of aluminium stearates, calcium linoleata pastes, hydrogenated castor oil, triglycerides, modified clays of bentonite type, polyol esters, silicas and polymers which are compatible with the mixture of monomers or of the same nature as the gelled polymer, such as some modified poly (acrylic acid)s, polymethacrylates or polyvinylpyrrolidone.

Another subject of the present invention is the various applications of the elastomer film according to the invention as coating for substrates, in particular made of elastomer or of plastic (gloves, fingerstalls, condoms, and the like) or for overformering a rubbing seal.

Figure 3:
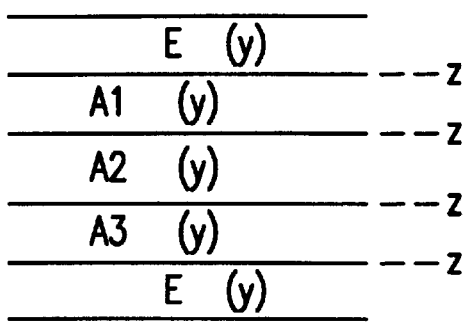
Figure 4:
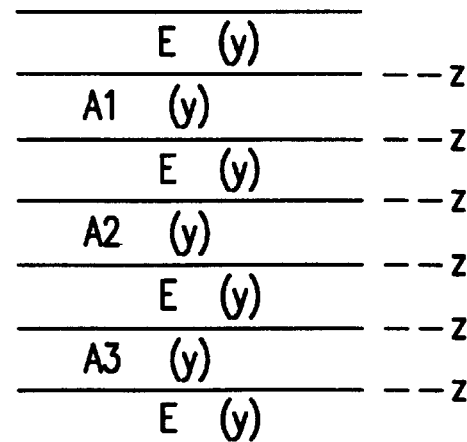
Figure 5:
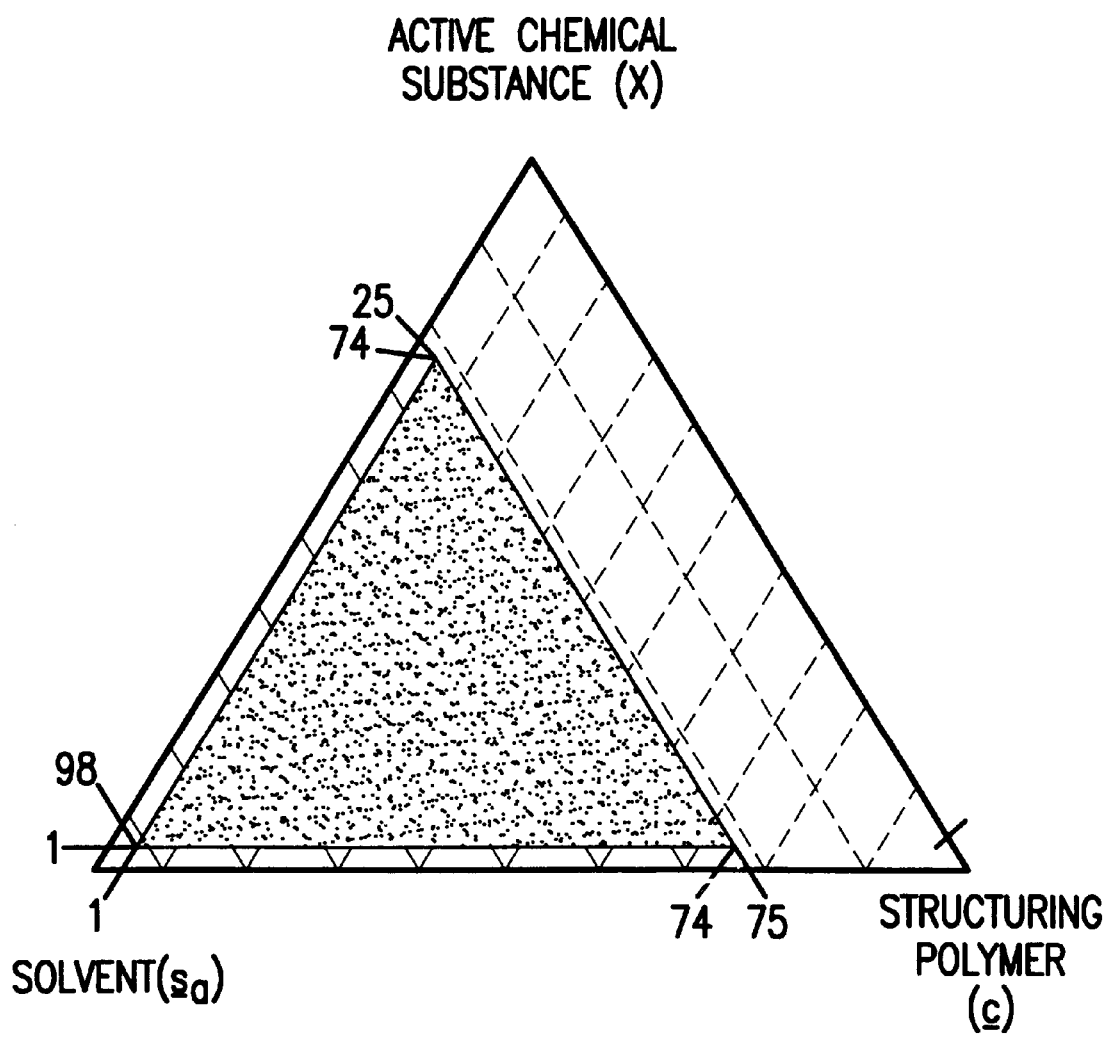
Figure 6:
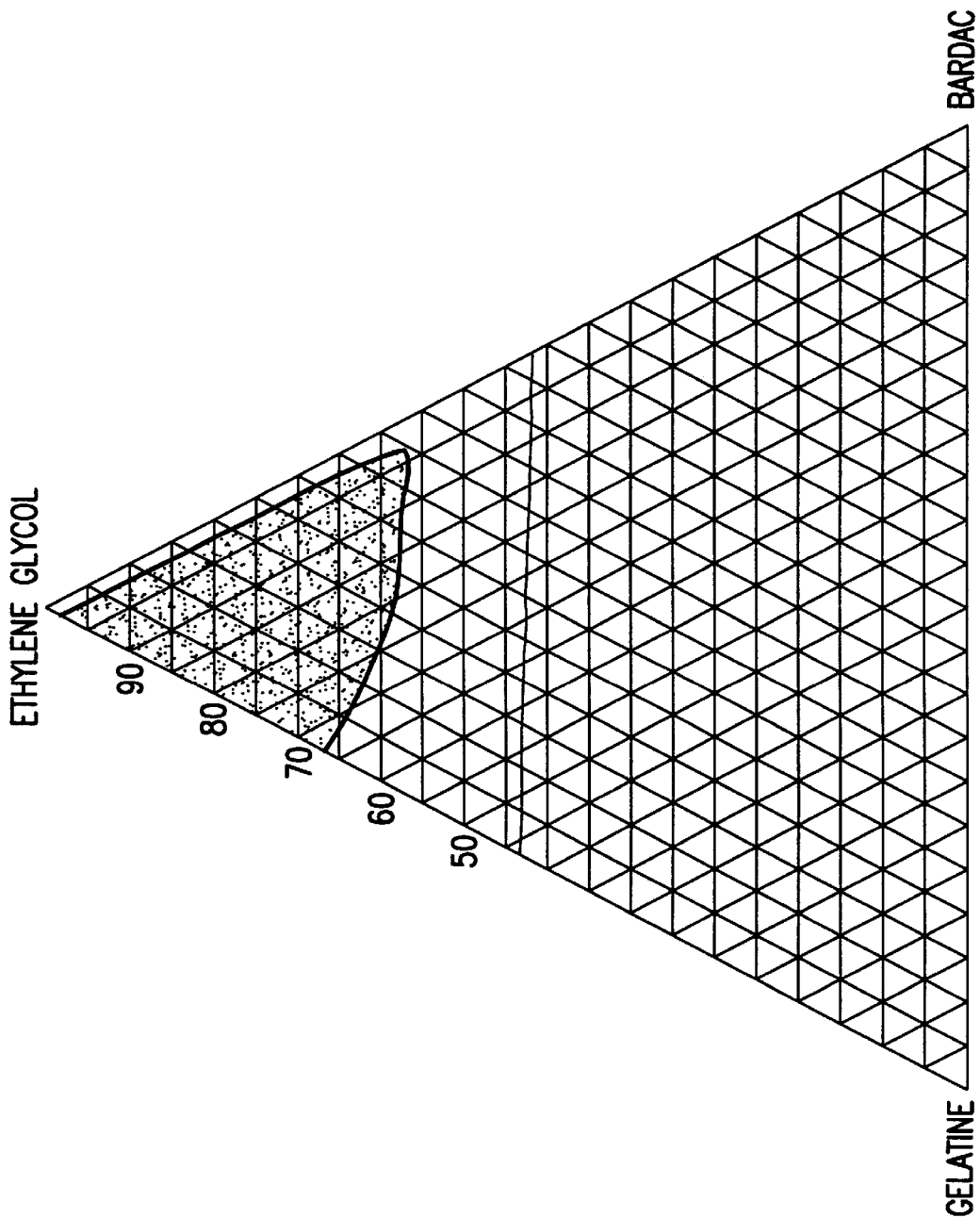

In addition to the preceding arrangements, the invention also comprises other arrangements which will emerge from the following description, which refers to implementational examples of the process which is the subject of the present invention and to the appended drawings, in which:

FIGS. 1 to 4 illustrate various embodiments of the multilayer material according to the invention in which the abbreviations c, e, x, ic, rc, $s_a$, $s_e$, $s_z$, y and z have the following meanings: c: structuring polymer c; e: elastomer e; x: active chemical substance x; rc: reversible crosslinking agent; ic: irreversible crosslinking agent; y: bonding agent y; z: polymer z providing the adhesion between two layers of different structures, and in which the brackets mean that the product is optionally present, FIG. 5 illustrates the combinations of the polymer c, active substance x and solvent $s_a$ mixture which make possible the preparation of a flexible and elastic layer (ternary diagram: delimitation of the range of existence of the gel): production of a reversible gel without crosslinking agent rc, in this figure, the grey-tinted range corresponds to the composition range claimed and FIG. 6 illustrates, by way of example, the ethylene glycol, Bardac® (dimethyldidecylammonium) and gelatin combinations which make possible the preparation of a flexible and elastic layer at room temperature (ternary diagram): delimitation of the range of existence of the gel: the hatched area corresponds to the range claimed.

However, it should be clearly understood that these examples are given solely by way of illustration of the subject of the invention, of which they do not in any way constitute a limitation.

Figure 2:
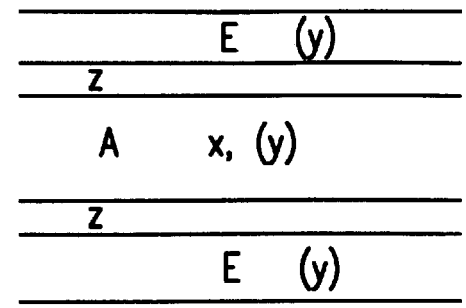

In accordance with the invention, such a multilayer polymeric film composed of a superimposition of layers can advantageously exhibit, in a non-limiting way, one of the following structures:

three-layered polymeric film comprising a layer A as a sandwich between two layers E (FIG. 1);

five-layered polymeric film comprising, successively, a layer E, a layer Z, a layer A, a layer Z and a layer E (FIG. 2);

five-layered polymeric film comprising, successively, a layer E, a layer A1, a layer A2, a layer A3 and a layer E (FIG. 3);

9-layered polymeric film comprising, successively, a layer E, a layer Z, a layer A1, a layer Z, a layer A2, a layer Z, a layer A3, a layer Z and a layer E (FIG. 3);

7-layered polymeric film comprising, successively, a layer E, a layer A1, a layer E, a layer A2, a layer E, a layer A3 and a layer E (FIG. 4);

13-layered polymeric film comprising, successively, a layer E, a layer Z, a layer A1, a layer Z, a layer E, a layer Z, a layer A2, a layer Z, a layer E, a layer Z, a layer A3, a layer Z and a layer E (FIG. 4).

In all these structures, both the layers A and the layers E can optionally contain a bonding agent y, whereas the layers A can, in addition, optionally comprise a crosslinking agent rc or ic (represented respectively by (y), (ic) and (rc) in the figures).

The layers A1, A2 and A3 can contain different concentrations of the same active chemical substances x or alternatively can each contain active chemical substances x of different nature.

EXAMPLE 1

Preparation of a Layer A which is Reversibly Crosslinked.

Gelatin resulting from collagen by acid treatment and with a Bloom value of 175 is dissolved, with stirring and at 60° C., in a mixture of didecyldimethylammonium chloride, sold by the company Lonza under the name of Bardac® 2270E (i.e. Bardac®), and ethylene glycol (or water) comprising 10% by mass of Bardac® with respect to the gel.

The clear solution formed contains 15% by mass of gelatin.

The temperature of the mixture (60° C.) corresponds to a temperature greater than the gel-liquid transition temperature, which is determined by a sudden variation in the viscosity of the mixture at this temperature and is, in the present case, 30–35° C.

The film A is obtained by cooling this solution, which is conditioned beforehand in the form of a film at 50° C. using a film drawer with a controlled thickness of 100 µm, or by cooling this solution on a ceramic former, according to the dipping principle.

The film A thus prepared possesses good elasticity and flexibility properties and properly retains the Bardac®.

EXAMPLE 2

Preparation of a Layer A which is Reversibly Crosslinked.

The preparation is carried out as for Example 1, the proportion of Bardac® being varied, however, between 5 and 25% with respect to the gel, the relative proportions of the other components remaining identical.

| BARDAC ® | ETHYLENE GLYCOL | GELATIN |
|---|---|---|
| 5 | 79.16 | 15.84 |
| 15 | 70.87 | 14.13 |
| 20 | 66.66 | 13.33 |
| 25 | 62.5 | 12.5 |

In all the cases, after film-forming and then cooling to a temperature of less than Ttrans, an elastic and flexible gel is obtained which properly retains the virucide.

These compositions are in agreement with the ternary diagrams according to FIGS. 5 and 6, obtained by carrying out the measurements at 25° C.

EXAMPLE 3
Preparation of a Layer A which is Reversibly Crosslinked.

The preparation is carried out as in Examples 1 and 2 above, the Bardac® being replaced by a polyvinylpyrrolidone-iodine complex sold by the company Aldrich under the reference 86,056-5.

Polyvinylpyrrolidone-iodine complex is thus dissolved, with stirring and at 60° C., in a mixture of water and gelatin, so as to obtain a solution comprising 5% by mass of polyvinylpyrrolidone-iodine complex.

The clear solution formed contains 15% by mass of gelatin.

The temperature of the mixture (60° C.) corresponds to a temperature greater than the gel-liquid transition temperature, which is determined by a sudden variation in the viscosity of the mixture at this temperature and is, in the present case, 30–35° C.

The film A is produced during the cooling of this solution, conditioned beforehand in the form of a film at 50° C. using a film drawer with a controlled thickness of 100 μm.

The film A thus prepared possesses good elasticity and flexibility properties and properly retains the virucide.

EXAMPLE 4
Preparation of a Layer A which is Reversibly Crosslinked.

In this example, the structuring polymer c is a polyacrylamide (PAAm) sold under the name N 300 by the Company Cytec. PAAm is dissolved with stirring, so as to obtain a 0.1–0.5% solution in water. The film A is obtained after evaporating the water on the ceramic former. The film obtained has good elastic properties.

EXAMPLE 5
Preparation of a 3-layered Multimaterial Possessing a Layer A which is Reversibly Crosslinked.

This example relates to the preparation of a simple multilayer material consisting of a layer A inserted between two barrier layers E.

Polyisoprene (PI) is dissolved, with stirring, in cyclohexane, so as to obtain a solution containing 15% by mass of PI.

A layer E with a thickness of 60 μm is prepared by coating a glass substrate with a solution of elastomer in cyclohexane using a film drawer with a controlled thickness of 200 μm. Two stages are necessary to do this, use being made of a 15% solution of polyisoprene in cyclohexane.

A layer A of 50 μm, which contains Bardac®, gelatin and ethylene glycol in the proportions 0.5/2/10, is added to this layer according to a process identical to that described in Examples 1 and 2.

A second elastomer barrier layer E with a thickness of 60 μm is then prepared on the layer A.

EXAMPLE 6
Preparation of a Layer A which is Reversibly Crosslinked.

In this example, the structuring polymer c is polyvinyl alcohol (PVA) of Mowiol® 26–88 type characterized by a percentage of hydrolysis of 88% and a viscosity of 26 mPa.s for a 4% solution in water at 20° C.

Mowiol® is dissolved, with stirring and at 80° C. in a water/PEG mixture, so as to obtain a solution containing 7.5% of Mowiol®Bardac® is added to this solution, so as to obtain a solution containing 76.5% of Bardac®.

The film A is obtained by dipping the ceramic former in the solution and by evaporation of the water at 70° C. The film obtained possesses good elastic properties.

EXAMPLE 7
Preparation of a 5-layered Multimaterial Possessing a Layer A which is Reversibly Crosslinked This example relates to the preparation of a multilayer material consisting of a layer A inserted between two barrier layers E, the adhesion being improved by a bonding layer Z.

As for Example 5, the layer E is prepared by dipping a former in a 15% solution of PI in cyclohexane. A bonding layer composed of SEBS treated with maleic anhydride and sold by the company Shell under the name of Kraton 1901, diluted to 15% of SEBS in cyclohexane, is added to this layer. After evaporating the solvent, the layer A, which is identical to that of Example 6, is obtained by dipping. A bonding layer and then a final elastomer layer are prepared in accordance with the above description.

EXAMPLE 8
Preparation of a 5-layered Multimaterial Possessing a Layer A which is Reversibly Crosslinked.

The preparation is carried out as in Example 7, the SEBS treated with maleic anhydride being replaced by a 3% acrylic acid/ethylene copolymer in toluene. This copolymer is sold under the name of Vamac® by the company Dupont or ATX® by the company Exxon.

EXAMPLE 9
Preparation of a 5-layered Multimaterial Possessing a Layer A which is Reversibly Crosslinked The preparation is carried out as in Example 20, the SEBS treated with maleic anhydride being replaced by a 3% methacrylate/styrene copolymer in toluene, sold under the name of Cyrolite® G20 by the company Huls.

EXAMPLE 10
Preparation of a 3-layered Multimaterial Possessing a Layer A which is Reversibly Crosslinked.

This example relates to the preparation of a multimaterial consisting of a layer A inserted between two barrier layers E, the adhesion being improved by means of a bonding agent y situated in the layer A.

The first elastomer layer is obtained as in the preceding examples. 3% of a butadiene-styrene-maleic anhydride copolymer, sold by the company Elf Atochem under the name of SMA 1440H, are added to the solution used for producing the layer A. The second barrier E is obtained as above.

EXAMPLE 11
Preparation of a 5-layered Multimaterial Possessing a Layer A, which is Reversibly Crosslinked, and a Bonding Layer Z.

This example relates to the preparation of a multilayer material consisting of a layer A inserted between two barrier layers E, the adhesion between the layers being improved by a bonding layer Z.

As for Example 5, a layer E with a thickness of 60 μm is prepared by coating a glass substrate with a solution of elastomer in cyclohexane using a film drawer with a controlled thickness of 200 μm. Two stages are necessary to do this, use being made of a 15% solution of polyisoprene in cyclohexane.

A bonding layer composed of an acrylic latex sold by the company Rohm & Haas under the name Primal® EP 6010 K, packaged in the form of an aqueous dispersion with a solids content of 55%, is added to this layer using a film drawer with a thickness of 50 μm.

After evaporation of the water at 50° C. in order to form the bonding layer, the layer A is applied at 50° C. using a film drawer with a thickness of 50 μm and then cooled until a flexible and elastic film is formed.

Finally, a bonding layer Z with a thickness of 50 μm and then a final elastomer layer E with a thickness of 60 μm are prepared in accordance with the above description.

The multimaterial obtained contains 5 layers and exhibits an acceptable elasticity, an acceptable flexibility and an acceptable interlayer adhesion.

EXAMPLE 12
Preparation of a 3-layered Multimaterial Possessing a layer A, which is Reversibly Crosslinked and a Bonding Agent y Incorporated in the Layer E.

This example relates to the preparation of a multilayer material consisting of a layer A inserted between two barrier layers E, the adhesion between the layers being improved by a bonding agent y introduced into the layer E.

Polyisoprene (PI) is dissolved, with stirring, in cyclohexane, 3o as to obtain a solution containing 15% by mass of PI.

A polybutadiene-block-polyoxyethylene di-block copolymer with a molecular mass of 51500 daltons and with a molar polyoxyethylene composition of 20% is added to this solution, so as to obtain a solution containing 5% of copolymer (expressed by mass with respect to the complete solution).

The film E with a thickness of 60 μm is obtained as described in Example 6 by evaporation of the solvent at 50° C.

A layer A of 50 μm and then a layer E of 60 μm are prepared in accordance with the description of Example 11 above.

The multimaterial contains 3 layers and exhibits an acceptable elasticity, an acceptable flexibility and an acceptable interlayer adhesion.

EXAMPLE 13
Preparation of a 3-layered Multimaterial Possessing a Layer A, which is Reversibly Crosslinked, and Comprising a Bonding Agent y Incorporated in the Layer A.

The preparation is carried out as in Example 12, the bonding agent, however, being introduced into the layer A.

Gelatin resulting from collagen by acid is treatment and with a Bloom value of 175 is dissolved, with stirring and at 60° C., in a mixture of Bardac® and ethylene glycol comprising 10% by mass of Bardac® with respect to the gel.

The clear solution formed contains 15% by mass of gelatin.

A grafted copolymer containing polyoxyethylene and acrylic chain members on an alkyl main chain, sold by the company Goldschmidt AG under the name Brinoil® LE 2362, is added to this solution.

The final solution contains 5% of grafted copolymer with respect to the gel.

The layer A is obtained by cooling this solution, conditioned beforehand in the form of a film at 50° C. using a film drawer with a controlled thickness of 50 μm.

The layers E of 60 μm on both sides of the layer A are prepared in a way analogous to the specifications presented in Example 11.

EXAMPLE 14
Preparation of a 6-layered Multimaterial Possessing Two Layers A, Comprising Two Different Virucides and Reversibly Crosslinked, and a Bonding Layer Z.

An elastomer layer E of 60 μm and then a bonding layer Z of 50 μm are prepared as in Example 11.

A first layer A of 50 μm is then added in accordance with Example 1, a mixture containing Bardac® as active chemical substance x being used.

A second layer A, also of 50 μm, is prepared in accordance with Example 3, a mixture containing polyvinylpyrrolidone-iodine complex as active chemical substance x being used.

The addition is than carried out, to this final layer A, of a bonding layer Z of 50 μm and then of a final elastomer layer E, as described in Example 11.

The multilayer material thus obtained exhibits an acceptable elasticity, an acceptable flexibility and an acceptable interlayer adhesion.

EXAMPLE 15
Preparation of a 3-layered Multimaterial Possessing a Layer A, which is Reversibly Crosslinked, and Comprising a Bonding Agent y Incorporated in the Layer A, which is Prepared According to an "Entirely Aqueous" Process.

The preparation is carried out as for Example 13 but with the solution of polyisoprene in cyclohexane being replaced by a prevulcanized natural rubber latex sold under the name of Revultex® LA, with a solids content of 60.5%.

Its viscosity at 20° C. is 70 mPa.s.

A layer E of 90 μm is prepared by coating a glass substrate with the prevulcanized latex using a film drawer with a controlled thickness of 150 μm.

After evaporating the water from the elastomer latex of the layer E and a vulcanization at 60° C., the layer A is applied in accordance with the description of Example 13 and then a final layer E is prepared.

The multilayer material thus obtained exhibits an acceptable elasticity, an acceptable flexibility and an acceptable interlayer adhesion.

EXAMPLE 16
Preparation of a 5-layered Multimaterial Possessing a Layer A, which is Reversibly Crosslinked, Comprising a Bonding Layer Z and Prepared According to an Entirely Aqueous Process.

The preparation is carried out as for Example 11, the prevulcanized natural rubber latex Revultex® LA being used.

A layer E of 90 μm is prepared by coating a glass substrate with the prevulcanized latex using a film drawer with a controlled thickness of 150 μm.

After evaporating the water from the elastomer latex of the layer E and a vulcanization at 60° C., a bonding layer Z of 50 μm of acrylic latex of Primal EP60-10 type is applied in accordance with the description of Example 11.

A layer A of 50 μm is then added in accordance with Example 1, a mixture containing Bardac® as active chemical substance x being used.

Finally, a bonding layer Z with a thickness of 50 μm and then a final elastomer layer E with a thickness of 90 μm are prepared in accordance with the above description.

The multilayer material thus obtained exhibits an acceptable elasticity, an acceptable flexibility and an acceptable interlayer adhesion.

EXAMPLE 17
Preparation of a 3-layered Multimaterial Possessing a Layer A which is Crosslinked by γ Radiation.

A solution containing 8% of PVP in water is prepared and is poured between two glass plates 1 mm apart. The system is positioned 31.5 cm from a $^{60}$Co source with an intensity of 0.66 rad/min for one month. The gel thus obtained possesses good flexibility.

EXAMPLE 18
Preparation of a 3-layered Multimaterial Possessing a Layer A which is Non-reversibly Crosslinked.

This example relates to the preparation of a multilayer material consisting of a layer A inserted between two barrier layers E, the layer A being crosslinked.

The first elastomer layer is obtained as in the Example 5. 3% of glutaraldehyde are added to the layer A according to Example 1. The second barrier E is obtained as above.

EXAMPLE 19
Preparation of a 3-layered Multimaterial Possessing a Layer A which is Non-reversibly Crosslinked.

This example relates to the preparation of a multilayer material consisting of a layer A inserted between two barrier layers E, the layer A being crosslinked.

The first elastomer layer is obtained as in the preceding examples. The layer A is obtained as in example 1 by dipping in a solution containing Bardac®, gelatine and ethylene glycol and then the former is immersed in a 0.3% solution of glutaraldehyde in acetone. After evaporation, the former is again immersed in the elastomer solution.

EXAMPLE 20
Preparation of a Layer A which is Non-reversibly Crosslinked.

In this example, the structuring polymer c is polyvinyl alcohol of Mowiol® 28–99 type, characterized by a molecular mass of 88000 daltons and a percentage of hydrolysis of 99%. Its viscosity, as a 4% solution in water at 20° C., is 28 mPa.s.

Mowiol® is dissolved in water (solvent $s_a$) with stirring and at 80° C., so as to obtain a 2.5% Mowiol® solution.

Triton X1000® (active chemical substance x) is added to this solution, with stirring, until a clear solution is obtained containing 10% of Triton (expressed with respect to the Mowiol® solution).

The clear solution obtained is provided in the form of a viscous liquid.

The solution containing the irreversible crosslinking agent ic is prepared by mixing glutaraldehyde in a water/hydrochloric acid mixture comprising 9 parts of water per one part of acid on a molar basis, so as to obtain a solution containing 0.005% of glutaraldehyde.

The layer A is prepared by simultaneously spraying 10 parts by mass of the solution containing Mowiol® with 0.0475 part by mass of the solution containing the irreversible crosslinking agent.

The layer A thus prepared exhibits an acceptable elasticity and an acceptable flexibility.

EXAMPLE 21
Preparation of a 3-layered Multimaterial Possessing a Layer A which is Reversibly Crosslinked, the Interlayer Adhesion of which is Provided by Treatment of the Elastomer Layer E.

This example relates to the preparation of a multilayer material consisting of a layer A inserted between two barrier layers E, the adhesion of which is obtained by a chemical treatment of the elastomer layer.

The elastomer layer is obtained by dipping a ceramic former in a 15% solution of a styrene-isoprene-styrene (SIS) (or styrene-butadiene-styrene (SBS)) copolymer in cyclohexane. After evaporating the solvent, the former is dipped in a 25 g/l solution of Oniachlor® (sold by the company Bostik) in water for 5 minutes.

Rinsing with ultrapure water makes it possible to remove the excess product. The layer A is then obtained as in Example 6. The final elastomer layer is added as in Example 5.

The adhesion of the layers is acceptable.

EXAMPLE 22
Preparation of a 3-layered Multimaterial in which the Layer A, which is Non-reversibly Crosslinked, is an Interpenetrated Network.

The first elastomer layer is obtained as in the preceding examples.

The preparation is carried out as in Example 1 as regards dissolving the gelatin. AAm, N,N'-bisacrylamide, crosslinking agent ic for the AAm, a redox initiator I and a crosslinking agent for the gelatin, ic', glutaraldehyde, are then added to the solution. The former is then dipped in this solution which contains Bardac®. After evaporating the water, covering is carried out with an SEBS layer as described above.

EXAMPLE 23
Preparation of a 3-layered Multimaterial in which the Layer A is Obtained by is Situ Polymerizaiton.

The elastomer layer E is prepared as in Example 5. The layer A is prepared by dipping the former in a mixture containing hydroxethyl methacrylate (HEMA), polyethylene glycol with a mass of 400 and Bardac®, in the proportions 1/1/1, being used; the polymerization being further initiated at 70° C., in the presence of $Na_2S_2O_5$ and $(NH_4)_2S_2O_8$. The final elastomer layer is added as in Example 5.

EXAMPLE 24
Preparation of a 3-layered Multimaterial in which the Layer A is Obtained by in Situ Polymerization in the Presence of Crosslinking Agent ic.

The elastomer layer E is prepared as in Example 5.

0.3% of ethylene glycol dimethacrylate (expressed with respect to the mass of polymer) is added as crosslinking agent ic to the mixture of Example 23.

The polymerization is initiated at 70° C. in the presence of AIBN.

A second elastomer barrier layer E is prepared on the layer A according to the dipping principle as described in Example 5.

EXAMPLE 25
Preparation of a 3-layered Multimaterial in which the Layer A is Obtained by is Situ Polymerization in the Presence of Crosslinked Agent ic.

The elastomer layer E is prepared as in Example 5. The layer A is added in accordance with Example 6, a mixture containing acrylamide, ethylene glycol, water N,N'-bisacrylamide (NBAAm) as crosslinking agent ic and Bardac® being used. The polymerization in initiated at room temperature in the presence of a redox initiator.

A second elastomer barrier layer E is prepared on the layer A, according to the dipping principle as described in Example 5.

EXAMPLE 26
Preparation of a 3-layered Multimaterial in which the Layer A is Obtained by in Situ Polymerization in the Presence of a Thickness f.

The elastomer layer E results from a dipping in a polychloroprene latex solution.

0.5% of silica is added as thickening agent f to the mixture of Example 23. The polymerization is initiated at 70° C. with benzoyl peroxide.

A second elastomer barrier layer E is prepared on the layer A by dipping the former in a 15% polyurethane solution.

EXAMPLE 27
Preparation of a 3-layered Multimaterial in which the Layer A is Obtained by in Situ Polymerization in the Presence of a Thickener f of the Same Chemical Nature as the Gel.

The barrier layer E is obtained by the same process as that of Example 5. A layer A, which contains HEMA, Bardac® and PEG according to the conditions of Example 23 in the proportions of 3/1/1, as wall as PHEMA, synthesized beforehand in bulk, in the presence of BP, is added to this layer according to the same process.

The final elastomer layer is added as in Example 5.

EXAMPLE 28
Preparation of a 5-layered Multimaterial in which the Layer A is Obtained by in Situ Polymerization in the Presence of Thickener f and in the Presence of a Bonding Layer Z.

The barrier layer E is obtained by the same process as that of Example 5. The former is then dipped in a Vamac solution and then in a solution containing HEMA, Bardac®, PEG, in the proportions 2/1/1, according to the conditions of Example 23, as well as BP (benzoyl peroxide) and poly (acrylic acid) sold by the company Protex under the name of Modarez 200.

After polymerization, the former is dipped in an elastomer solution B as described above.

EXAMPLE 29
Preparation of a 5-layered Multimaterial in which the Layer A is Obtained by in Situ Polymerization and which Comprises a Bonding Layer Z.

The barrier layer E is obtained by the same process as that of Example 5. A bonding layer consisting of a latex of acrylic, sold under the name of Primal EP 6010K, is added to this layer according to the same process. After drying, the layer A is deposited according to the dipping principle. It results from the mixing of 0 to 50% of methyl methacrylate with 100 to 50% of hydroxyethyl methacrylate in the presence of water, Bardac® and PEG 400.

Initiation is achieved with BP at 70° C. After obtaining the gel, the former is again immersed in the Primal solution before being covered with a second barrier layer E as described in Example 5.

EXAMPLE 30
Preparation of a 3-layered Multimaterial in which the Layer A is Obtained by in Situ Polymerization Initiated by UV Radiation.

The barrier layer E is obtained by the same process as that of Example 5. An HEMA/NVP (N-vinylpyrrolidone) (70/30) mixture is added to this layer, according to the same process, in the presence of an initiator i, 2-hydroxy-2,2-dimethylacetophenone (Darocur® 1173), and of a solvent $s_a$, glycerol.

The polymerization is initiated by UV radiation ($\gamma$=365 nm) for 2 hours. After obtaining the gel, the former is dipped in an elastomer solution E as described above.

EXAMPLE 31
Preparation of a 4-layered Multimaterial Possessing a Layer A which is Non-reversibly Crosslinked, the Interlayer Adhesion of which is Provided by a Treatment of the Elastomer Layer E.

This example relates to the preparation of a multilayer material composed of a layer A inserted between two barrier layers E, the adhesion of which is provided by a plasma treatment of the elastomer layer E, on one side, and by a bonding layer Z, on the other side.

The elastomer layer E is obtained by dipping a ceramic former in a 15% SBS or SIS solution in accordance with Example 5.

The former is placed in a chamber into which is passed ionized nitrogen, argon or oxygen gas, so as to oxidize the surface. The improvement in the wettability of the elastomer provides good adhesion with the layer obtained as in Example 5. The former is then dipped in a solution of gelatine, Bardac® and ethylene glycol (as described in example 5), then in a solution at 0.3% of glutaraldehyde in acetone and then covered with an elastomer layer E as described above.

In addition to that which emerges from the above, the invention is in no way restricted to those of its implementations, embodiments and application modes which have just been described more explicitly; on the contrary, it embraces all the variants thereof which can come to the mind of a technologist in the subject, without departing from the context or from the scope of the present invention.

What is claimed is:

1. A multilayer polymer material, which comprises:
   at least one continuous layer A composed of a gel which is irreversible as a function of the temperature, which comprises at least one active chemical substance x, a structuring polymer c, a crosslinking agent ic selected from the group consisting of aldehydes, dialdehydes, and prepolymers containing isocyanate functional groups, and a solvent $s_a$; and
   at least two barrier layers E which comprise a synthetic elastomer e,
   said layers A and E being held together by: a polymeric bonding agent y incorporated in at least one of said layers A or E.

2. The multilayer material according to claim 1, wherein the structuring polymer c of the layer A is a polymer which is immiscible with the synthetic elastomer e, and which is compatible with the active chemical substance x and/or the solvent $s_a$.

3. The multilayer material according to claim 1, wherein the said polymeric bonding agent y is incorporated into said layer A.

4. The multilayer material according to claim 1, wherein the structuring polymer c is a synthetic polymer selected from the group consisting of (a) polyethyleneimine, (b) poly(acrylic acid), (c) polyvinyl alcohol, (d) polyacrylamide, (e) polyvinylpyrrolidone, (f) poly(vinyl ether); and (g) a derivative of any of (a)–(f).

5. The multilayer material according to claim 1, wherein the active chemical substance x is a compound capable of causing an essentially instantaneous denaturation of proteins on simple contact by a chemical reaction or by a physico-chemical effect.

6. The multilayer material according to claim 5, wherein said physicochemical effect is a modification of surface tension.

7. The multilayer material according to claim 5, wherein said chemical substance x is a biocide.

8. The multilayer material according to claim 7, wherein said biocide is selected from the group consisting of (a) a quaternary ammonium, (b) a biguanide, (c) a phthalaldehyde, (d) a phenol derivative, (e) formaldehyde, (f) a non-ionic surfactant containing at least one polyoxyethylene sequence, (g) hexamidine, (h) an iodinated compound, (i) a virucidally active non-ionic surfactant, (j) sodium or potassium dichromate or hypochlorite, and (k) a mixture of any of (a)–(j).

9. The multilayer material according to claim 8, wherein said quaternary ammonium is dimethyldidecylammonium chloride, or said iodinated compound is a polyvinylpyrrolidone-iodine complex.

10. The multilayer material according to claim 1, wherein the solvent $s_a$ for the layer A is selected from the group consisting of (i) a polyol or a polyethylene glycol which is liquid at room temperature and has a molecular weight of between about 62 Da and 750 Da; and (ii) a volatile solvent, the solvents (i) and (ii) being used alone or as mixtures.

11. The multilayer material according to claim 10, wherein said polyol or polyethylene glycol is ethylene glycol, propylene glycol or glycerol, and wherein said volatile solvent is an alcohol, a ketone, an ether, a dimethylformamide, dimethyl sulphoxide or water.

12. The multilayer material according to claim 1 wherein the bonding agent y is selected from the group consisting of:
(i) polymers containing both at least one poly A sequence compatible with the layer A and at least one poly E sequence compatible with the layer E which are selected from the group consisting of:
di-block copolymers of formula poly A-block-poly E,
tri-block copolymers of formulas poly E-block-poly A-block-poly E (EAE), poly A-block-poly E-block-poly A (AEA), poly A-block-poly E-block-poly F (AEF) or poly A-block-poly F-block-poly E (AFE), and
grafted copolymers of formulas poly A-grafted-poly E, poly E-grafted-poly A, or poly A-grafted-poly E and -poly F, it being possible for the poly F sequence to be compatible with the layer A or with the layer E.

13. The multilayer material according to claim 1, wherein the gel layer A comprises:
between 0 and 98% of solvent $s_a$ with respect to the gel,
between 0.1 and 74% of structuring polymer c with respect to the gel,
between 1 and 80% of the active chemical substance x with respect to the gel, and
between 0.0001 and 0.1% by weight of crosslinking agent ic per combined other constituents.

14. The multilayer material according to claim 13, wherein said gel layer A comprises between 25% and 98% of the solvent $s_a$ with respect to the gel.

15. The multilayer material according to claim 13, wherein said gel layer A comprises between 1% and 74% of the structuring polymer c with respect to the gel.

16. The multilayer material according to claim 13, wherein said gel layer A comprises between 1% and 74% of the active chemical substance x with respect to the gel.

17. The multilayer material according to claim 13, wherein, when the gel layer A additionally comprises a bonding agent y, the proportions by weight of the latter are between 0.01 and 25% with respect to the gel, the proportions of solvent $s_a$ being consequently adjusted.

18. The multilayer material according to claim 1, wherein the elastomer layers E comprise a synthetic elastomer e selected from the group consisting of polybutadiene, polyisoprene, an acrylic polymer, polychloroprene, polyurethane, a chlorobutadiene-methacrylic acid copolymer, an ethylene vinyl acetate copolymer, a styrene butadiene rubber (SBR) copolymer, a styrene-butadiene-styrene (SBS) copolymer, a styrene-isoprene-styrene (SIS) copolymer and a styrene-ethylene-butylene-styrene (SEBS) copolymer, and said polymeric bonding agent y is incorporated into said layers E.

19. A glove coated with a multilayer material according to claim 1.

20. A fingerstall coated with a multilayer material according to claim 1.

21. A condom coated with a multilayer material according to claim 1.

22. A multilayer polymer material, which comprises:
(a) at least one continuous layer A composed of a gel which is irreversible as a function of the temperature, which comprises at least one active chemical substance x, a structuring polymer c, a crosslinking agent ic and a solvent $s_a$; and
(b) at least two barrier layers E which comprise a synthetic elastomer e, said layers A and E being held together by a polymeric bonding agent y incorporated in at least one of said layers A or E; wherein the bonding agent y is selected from the group consisting of:
(i) polymers containing both at least one poly A sequence compatible with the layer A and at least one poly E sequence compatible with the layer E which are selected from the group consisting of:
(a) di-block copolymers of formula poly A-block-poly E;
(b) tri-block copolymers of formulas poly E-block-poly A-block-poly E (EAE), polyA-block-poly E-block-polyA (AEA), poly A-block E-block poly F (AEF) or poly A-block-poly F-block-poly E (AFE); and
(c) grafted copolymers of formulas poly A-grafted-poly E, poly E-grafted-poly A, or poly A-grafted-poly E and -poly F, it being possible for the poly F sequence to be compatible with the layer A or with E; wherein the poly A sequences are selected from the group consisting of polyoxyethylene, polyvinylpyridine, poly(acrylic acid)s, polyvinyl alcohol and quaternized polyvinylpyridine and the poly E sequences are selected from the group consisting of polydienes, polyolefins, polyoxypropylene and polydimethylsiloxane.

23. The multilayer material according to claim 22, wherein the structuring polymer c of the layer A is a polymer which is immiscible with the synthetic elastomer e and which is compatible with the active chemical substance x and/or solvent $s_a$.

24. The multilayer material according to claim 22, wherein the said irreversible gel additionally contains a bonding agent y.

25. The multilayer material according to claim 22, wherein the structuring polymer c is a synthetic polymer selected from the group consisting of (a) polyethyleneimine, (b) poly(acrylic acid), (c) polyvinyl alcohol, (d) polyacrylamide, (e) polyvinylpyrrolidone, (f) poly(vinyl ether); and (g) a derivative of any of (a)–(f).

26. The multilayer material according to claim 22, wherein the crosslinking agent ic is selected from the group consisting of aldehydes, dialdehydes, and prepolymers containing isocyanate functional groups.

27. The multilayer material according to claim 22, wherein the active chemical substance x is a compound capable of causing an essentially instantaneous denaturation of proteins upon simple contact by a chemical reaction or by a physicochemical effect.

28. The multilayer material according to claim 27, wherein said physicochemical effect is a modification of surface tension.

29. The multilayer material according to claim 27, wherein said chemical substance x is a biocide.

30. The multilayer material according to claim 29, wherein said biocide is selected from the group consisting of (a) a quaternary ammonium, (b) a biguanide, (c) a phthalaldehyde, (d) a phenol derivative, (e) formaldehyde, (f) a non-ionic surfactant containing at least one polyoxyethylene sequence, (g) hexamidine, (h) an iodinated compound, (i) a virucidally active non-ionic surfactant, (j) sodium or potassium dichromate or hypochlorite, and (k) a mixture of any of (a)–(j).

31. The multilayer material according to claim 30, wherein said quaternary ammonium is dimethyldidecylammonium chloride, and said iodinated compound is a polyvinylpyrrolidone-iodine complex.

32. The multilayer material according to claim 22, wherein the solvent $s_a$, for the layer A is selected from the group consisting of (i) a polyol or a polyethylene glycol which is liquid at room temperature and has a molecular weight of between about 62 Da and 750 Da; and (ii) a volatile solvent, the solvents (i) and (ii) being used alone or as mixtures.

33. The multilayer material according to claim 32, wherein said polyol or polyethylene glycol is ethylene glycol, propylene glycol or glycerol, and wherein said volatile solvent is an alcohol, a ketone, an ether, a dimethylformamide, dimethyl sulfoxide or water.

34. The multilayer material according to claim 22, wherein said gel layer A comprises:
   between 0% and 98% of the solvent $s_a$ with respect to the gel,
   between 0.1% and 74% of the structuring polymer c with respect to the gel.
   between 1% and 80% of the active chemical substance x with respect to the gel, and
   between 0.0001% and 0.1% by weight of crosslinking agent ic per combined other constituents.

35. The multilayer material according to claim 34, wherein said gel layer A comprises between 25% and 98% of the solvent $s_a$ with respect to the gel.

36. The multilayer material according to claim 34, wherein said gel layer A comprises between 1% and 74% of the structuring polymer c with respect to the gel.

37. The multilayer material according to claim 34, wherein said gel layer A comprises between 1% and 74% of the active chemical substance x with respect to the gel.

38. The multilayer material according to claim 34, wherein, when the bonding agent y is incorporated in the gel layer A the proportions by weight of said bonding agent y are between 0.01 and 25% with respect to the gel, the proportions of solvent $s_a$ being consequently adjusted.

39. The multilayer material according to claim 22, wherein the elastomer layers E comprise a synthetic elastomer e selected from the group consisting of polybutadiene, polyisoprene, acrylic polymers, polychloroprene, polyurethane, chlorobutadiene-methacrylic acid copolymers, ethylene-vinyl acetate copolymers, styrene butadiene rubber (SBR) copolymers, styrene-butadiene-styrene (SBS) copolymers, styrene-isoprene-styrene (SIS) copolymers, styrene-ethylene-butylene-styrene (SEBS) copolymers, and said polymeric bonding agent y is incorporated into said layers E.

40. A glove coated with a multilayer material according to claim 22.

41. A fingerstall coated with a multilayer material according to claim 22.

42. A condom coated with a multilayer material according to claim 22.

* * * * *